United States Patent
Mario et al.

(10) Patent No.: US 6,661,867 B2
(45) Date of Patent: Dec. 9, 2003

(54) TOMOGRAPHIC SCANNING X-RAY INSPECTION SYSTEM USING TRANSMITTED AND COMPTON SCATTERED RADIATION

(75) Inventors: Arthur W. Mario, Hopatcong, NJ (US); Scott D. Kravis, West Caldwell, NJ (US)

(73) Assignee: Control Screening, LLC, Fairfield, NJ (US)

( * ) Notice: Subject to any disclaimer, the term of this patent is extended or adjusted under 35 U.S.C. 154(b) by 0 days.

(21) Appl. No.: 10/036,953

(22) Filed: Oct. 19, 2001

(65) Prior Publication Data

US 2003/0076924 A1 Apr. 24, 2003

(51) Int. Cl.$^7$ ............................. G01N 23/04; G01T 1/20
(52) U.S. Cl. ..................... 378/57; 378/90; 250/367; 250/368
(58) Field of Search ..................... 378/57, 86, 88, 378/89, 90; 250/367, 368

(56) References Cited

U.S. PATENT DOCUMENTS

| | | | | |
|---|---|---|---|---|
| 3,944,833 A | * | 3/1976 | Hounsfield | 250/367 |
| 4,392,237 A | | 7/1983 | Houston | 378/51 |
| 4,437,006 A | | 3/1984 | Morgan et al. | 250/363 |
| 4,495,084 A | * | 1/1985 | Shimizu et al. | 252/301.17 |
| 4,651,002 A | * | 3/1987 | Anno | 250/336.1 |
| 4,792,900 A | * | 12/1988 | Sones et al. | 600/407 |
| 4,799,247 A | | 1/1989 | Annis et al. | 378/87 |
| 4,817,121 A | | 3/1989 | Shimizu et al. | 378/57 |
| 4,893,015 A | * | 1/1990 | Kubierschky et al. | 250/369 |
| 4,918,315 A | | 4/1990 | Gomberg et al. | 250/390.04 |
| 4,974,247 A | | 11/1990 | Friddell | 378/90 |
| 5,012,103 A | * | 4/1991 | Tanaka et al. | 250/368 |
| 5,033,073 A | | 7/1991 | Friddell | 378/146 |
| 5,181,234 A | | 1/1993 | Smith | 378/87 |
| 5,247,561 A | | 9/1993 | Kotowski | 378/87 |
| 5,260,981 A | | 11/1993 | Uyama | 378/57 |
| 5,260,982 A | | 11/1993 | Fujii et al. | 378/87 |
| 5,313,511 A | | 5/1994 | Annis et al. | 378/87 |
| 5,404,387 A | | 4/1995 | Hammond et al. | 378/98.3 |
| 5,428,657 A | | 6/1995 | Papanicolopoulos et al. | 378/86 |
| 5,514,870 A | * | 5/1996 | Langenbrunner | 250/367 |
| 5,550,378 A | * | 8/1996 | Skillicorn et al. | 250/367 |
| 5,600,700 A | | 2/1997 | Krug et al. | 378/57 |
| 5,642,393 A | | 6/1997 | Krug et al. | 378/57 |
| 5,763,886 A | | 6/1998 | Schulte | 250/358.1 |
| 5,917,880 A | | 6/1999 | Bjorkholm | 378/57 |
| 5,930,314 A | * | 7/1999 | Lanza | 376/159 |
| 5,940,468 A | | 8/1999 | Huang et al. | 378/57 |
| 5,943,388 A | | 8/1999 | Tümer | 378/98.9 |
| 5,949,842 A | | 9/1999 | Schafer et al. | 378/4 |
| 5,956,382 A | * | 9/1999 | Wiener-Avnear et al. | 378/98.8 |
| 5,969,806 A | | 10/1999 | Bergano | 356/73.1 |
| 6,018,562 A | | 1/2000 | Willson | 378/9 |
| 6,058,159 A | | 5/2000 | Conway et al. | 378/68 |
| 6,081,580 A | | 6/2000 | Grodzins et al. | 378/87 |
| 6,087,663 A | * | 7/2000 | Moisan et al. | 250/367 |
| 6,122,344 A | * | 9/2000 | Beevor | 378/88 |
| 6,151,381 A | | 11/2000 | Grodzins et al. | 378/90 |
| 6,192,101 B1 | * | 2/2001 | Grodzins | 378/55 |
| 6,246,744 B1 | * | 6/2001 | Duclos et al. | 378/19 |
| 6,269,142 B1 | * | 7/2001 | Smith | 378/57 |

OTHER PUBLICATIONS

Eriksson et al. , Nucl. Instrum. Meth. 122, 373 (1974).*
Becker et al., Nucl. Instrum. Meth. 123, 199 (1975).*

* cited by examiner

*Primary Examiner*—Edward J. Glick
*Assistant Examiner*—Allen C Ho
(74) *Attorney, Agent, or Firm*—Ernest D. Buff & Associates, LLC; Ernest D. Buff; Gordon E. Fish (57) ABSTRACT

X-ray radiation is transmitted through and scattered from an object under inspection to detect weapons, narcotics, explosives or other contraband. Relatively fast scintillators are employed for faster X-ray detection efficiency and significantly improved image resolution. Detector design is improved by the use of optically adiabatic scintillators. Switching between photon-counting and photon integration modes reduces noise and significantly increases overall image quality.

25 Claims, 9 Drawing Sheets

TOMOGRAPHIC SCANNING X-RAY INSPECTION SYSTEM USING TRANSMITTED AND COMPTON SCATTERED RADIATION

BACKGROUND OF THE INVENTION

1. Field of the Invention

The present invention relates to X-ray screening systems for airport luggage and the like; and, more particularly to screening systems that utilize radiation transmitted through and scattered from an object under inspection to detect weapons, narcotics, explosives or other contraband.

2. Description of the Prior Art

X-ray inspection systems that use transmitted radiation have conventionally been employed to detect the shape of high-Z material (Z refers to atomic number) such as steel. The principle objective of these systems is the detection of weapons, such as guns, knives, bombs and the like. A major problem with X-ray inspection systems is the inability thereof to accurately recognize and detect explosives and narcotics made up of low-Z materials. Recently dual energy X-ray systems have been used to improve the detection of low-Z material. Such systems measure the different attenuation that high and low transmitted energy X-rays experience as a result of passage through any material. This principal has allowed the identification of virtually any material so long as the material is not covered by a different Z material. In order to overcome the material overlaying problem, it has been proposed that X-ray transmission be effected from different directions using two X-ray sources, or that the object be scanned from all sides and the results be evaluated with computer tomography.

Another approach for identifying low-Z material involves detecting the Compton scattered radiation along with the transmitted radiation. Low-Z material such as explosives and narcotics generates more scattered radiation than high-Z material like iron. This scattered radiation differential provides a basis for distinguishing between low-Z and high-Z material in instances where the low-Z material is concealed behind high-Z material.

Among the more troublesome problems with X-ray transmission and Compton scatter images are their poor resolution and high noise content. The causes of these problems are traced to: a) the relatively poor light collection method used in converting X-ray photons to light photons; and b) photon integration. Poor light collection presents a problem because it requires use of slow (long persistence) phosphor type X-ray detectors. Such detectors oftentimes create blurred images owing to the slow response time of the excited phosphor. The use of photon integration in conventional signal generation produces noisy images, particularly in cases where the transmitted or backscattered X-ray rates are relatively small. For example, U.S. Pat. No. 5,260,982 to Fujii et al. discloses a scattered radiation imaging apparatus. The Fujii et al. apparatus employs long persistence phosphor type X-ray detectors and photon integration yielding relatively low resolution, high noise images.

Employing relatively fast (very short persistence) phosphors such as $Gd_2SiO_5$ or $Y_2O_2Si$, or an organic plastic scintillator (loaded or unloaded with lead or tin), for faster X-ray detection efficiency, would significantly improve image resolution. When coupled with photon-counting electronics to reduce noise, overall image quality would be significantly improved. These improvements would yield a sharper image more capable of recognizing bombs, currency, narcotics and other contraband shapes and accompaniments.

SUMMARY OF THE INVENTION

The present invention provides a system and method for X-ray inspection of an object to detect weapons, narcotics, explosives or other contraband.

When an X-ray photon is absorbed by the scintillator, the scintillator generates photons in the visible part of the spectrum. These photons travel down the scintillator and enter a photon detector, such as a photomultiplier, that is coupled to the scintillator. The photomultiplier effectively converts the photons to electrons that can be processed by electronics for image generation. For the backscatter detector, the X-ray signals will be processed in the counting mode where individual X-rays are counted to generate the Compton backscatter image. For the transmitted beam image, the number of X-ray photons that enter the scintillator can vary over a wide dynamic range that is dependent on the object under inspection. In the case where there is no object or a very weak absorbing object the X-ray rate on the scintillator can be so high that counting individual X-rays is not possible. On the other extreme, for a highly attenuating object the X-ray rate would be very low or even zero. To accommodate this wide range of X-ray rates, the transmission detector system operates in a combined mode comprised of photon counting and photon integrating modes, where the mode is dynamically selected depending on the X-ray rate. This optimized method of collecting X-ray signals yields a superior image, as opposed to using only photon counting or photon integration.

The spatial resolution in the horizontal plane is accomplished via a pencil beam scanning across the inspection tunnel while a conveyor moves the object through the inspection tunnel. As only one line through the object is excited by the pencil beam at any time, the radiation captured by any scintillation detector is independent from the locus of the scintillation material that is actually hit by an X-ray photon, and must originate from this pencil line. The location of the pencil beam within the object image can be derived from the conveyor moving the object and the rotating disk with apertures that generate the pencil beam. It is possible to generate a direct luminescent image of an object with the transmission detector and an enhanced low Z image from the backscatter detectors and display them on separate monitors.

Preferably, the images produced by the transmission detector and backscatter detector are displayed as adjacent windows of the same monitor. Signal information from the transmission detector is used to correct for attenuation effects in the backscatter images, thereby avoiding artifacts in the low Z images produced by attenuation due to high Z objects. Conversely, signal information from the backscatter detectors can be used to correct for scatter effects in the transmission image, thereby avoiding artifacts in the high Z image produced by scattering attenuation due to low Z objects. By means of these corrections a greater fraction of the image on the high Z window display is derived from absorption effects of high Z objects, and a greater fraction of the image on the low Z window display is derived from scattering effects of low Z objects. Accordingly, the images displayed by the high Z and low Z windows are more distinct.

Tomographic information can optionally be obtained by using additional Compton backscatter detectors. Backscattered X-rays originating from elements close to the bottom of the object hit mainly the scintillator next to the entrance slit, while backscatter from elements further up the pencil beam hit all backscatter scintillation detectors nearly equally. Photon collection efficiency is improved and real-time image noise is reduced, when compared to collimation methods that limit angular admittance of photons. The tomographic zones can be displayed in windowed sections on a single monitor or on separate monitors.

With at least one additional detector overlaying the extant transmission detector, or by dividing the extant transmission detector into low energy and high energy components, dual energy information can be obtained. This information can be displayed as a dual energy image, which is color coded to designate the atomic number of an object under inspection. A single energy image yields only object radiographic density information, as contrasted to a dual energy image, which yields radiographic density and atomic number, Z, of the object under inspection. Combining the information from the backscatter data and dual energy data can further enhance discrimination of different materials and aid in the separation of overlaying materials of different atomic number Z.

By employing relatively fast scintillators for faster X-ray detection efficiency, the present invention significantly improves image resolution. Detector design is improved by the use of optically adiabatic scintillators. The system switches between photon-counting and photon integration modes to reduce noise and significantly increase overall image quality. In addition, the system automatically adjusts belt speed (i) to allow rapid entrance into the inspection zone, (ii) slow traverse through the inspection zone to prolong residence therein of articles appointed for inspection, and (iii) allow rapid exit from the inspection zone. This automatic belt speed adjustment feature affords increased resolution and reduced noise with minimum speed penalty. Advantageously, the system provides a sharper image that is more capable of recognizing bombs, currency, narcotics and other contraband shapes and accompaniments.

BRIEF DESCRIPTION OF DRAWINGS

The invention will be more fully understood and further advantages will become apparent when reference is had to the following detailed description and the accompanying drawings, in which.

DESCRIPTION OF THE PREFERRED EMBODIMENTS

The invention provides an apparatus and method for X-ray inspection systems that utilize radiation transmitted through and scattered from the object under inspection to detect weapons, narcotics, explosives or other contraband.

Figure 1:
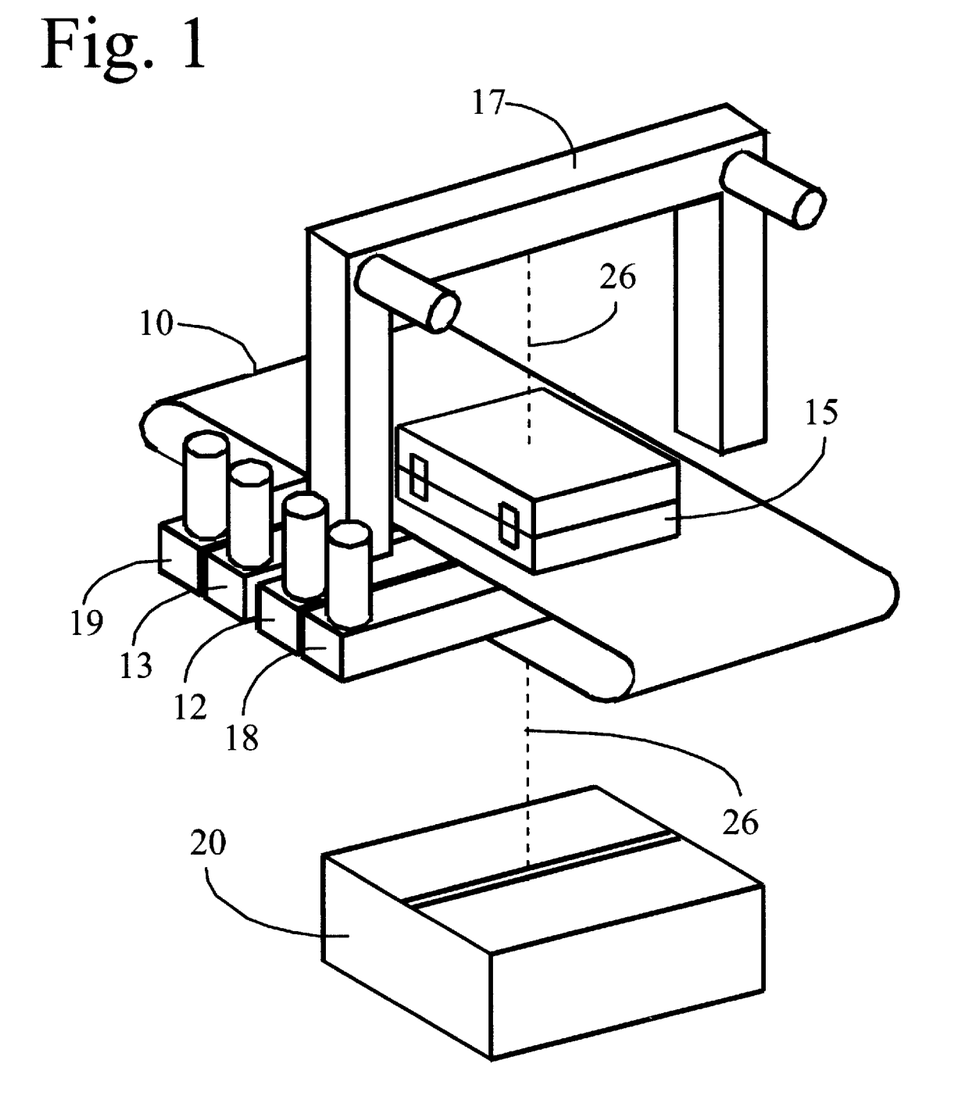
FIG. 1 is a perspective view depicting an overview of an X-ray inspection system using transmitted and Compton backscattered radiation.
Figure 2:
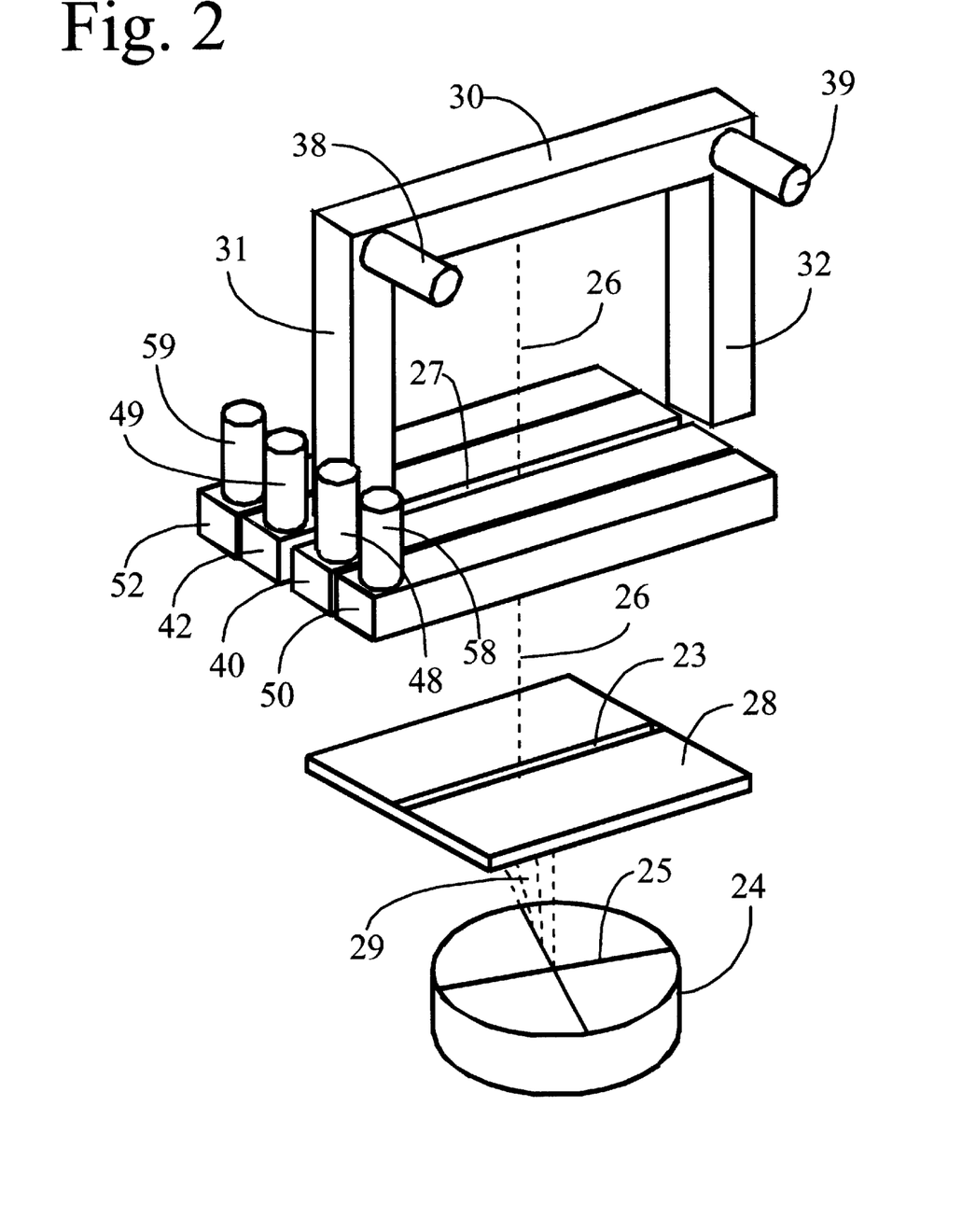
FIG. 2 is a perspective view showing the arrangement of x-ray generator and pencil beam shaping components of the detector of FIG. 1.

Specifically, as shown in FIGS. 1 and 2, the invention provides a tomographic scanning X-ray inspection system. The system has conveyor 10 for moving object 15 to be scanned though the system. An X-ray generation device 20 generates a pencil beam of X-rays 26. Pencil beam 26 is repeatedly swept along pencil beam entrance slit 27 across conveyor 10. The scanning direction of the pencil beam 26 is substantially perpendicular to the object's movement. In this manner, object 15 is repeatedly scanned as it moves on conveyor 10. X-ray generation device 20 is known in the art and generally comprises an X-ray tube within or behind rotating wheel 24 having a plurality of slits 25 from which a fan of X-rays 29 are emitted. X-ray shield 28 is provided with slit 23 from which pencil beam 26 emerges.

Alternatively, the wheel is vertical and provided with holes along its rounded side such that a beam of X-rays is swept along the object. This pencil beam originates from an x-ray source, which emits radiation into cone. A rotating lead covered wheel with four small holes 90 degree apart, makes this conical radiation into a scanning pencil beam. One rotation of the wheel will result in four pencil beam passes through the object under inspection.

Fast backscatter detectors 12 and 13 generate a backscatter signal when detecting X-rays backscattered by object 15. The fast backscattered detectors 12 and 13 are positioned on the same side of the moving object 15 as the X-ray generation device 20 and across from each other and proximate to pencil beam entrance slit 27. Preferably, the fast backscatter detectors 12 and 13 are proximate to (and more preferably, substantially parallel to) pencil beam entrance slit 27 and are comprised of scintillators 40 and 42 and photon detectors 48 and 49 respectively. Scintillators 40 and 42 are comprised of organic plastic. Photon detectors 48 and 49 are preferably photomultipliers. Alternatively, scintillators 40 and 42 are comprised of short persistence phosphor such as $Gd_2SiO_5$ or $Y_2O_2Si$. Optionally, only one backscatter detector is used.

Figure 3:
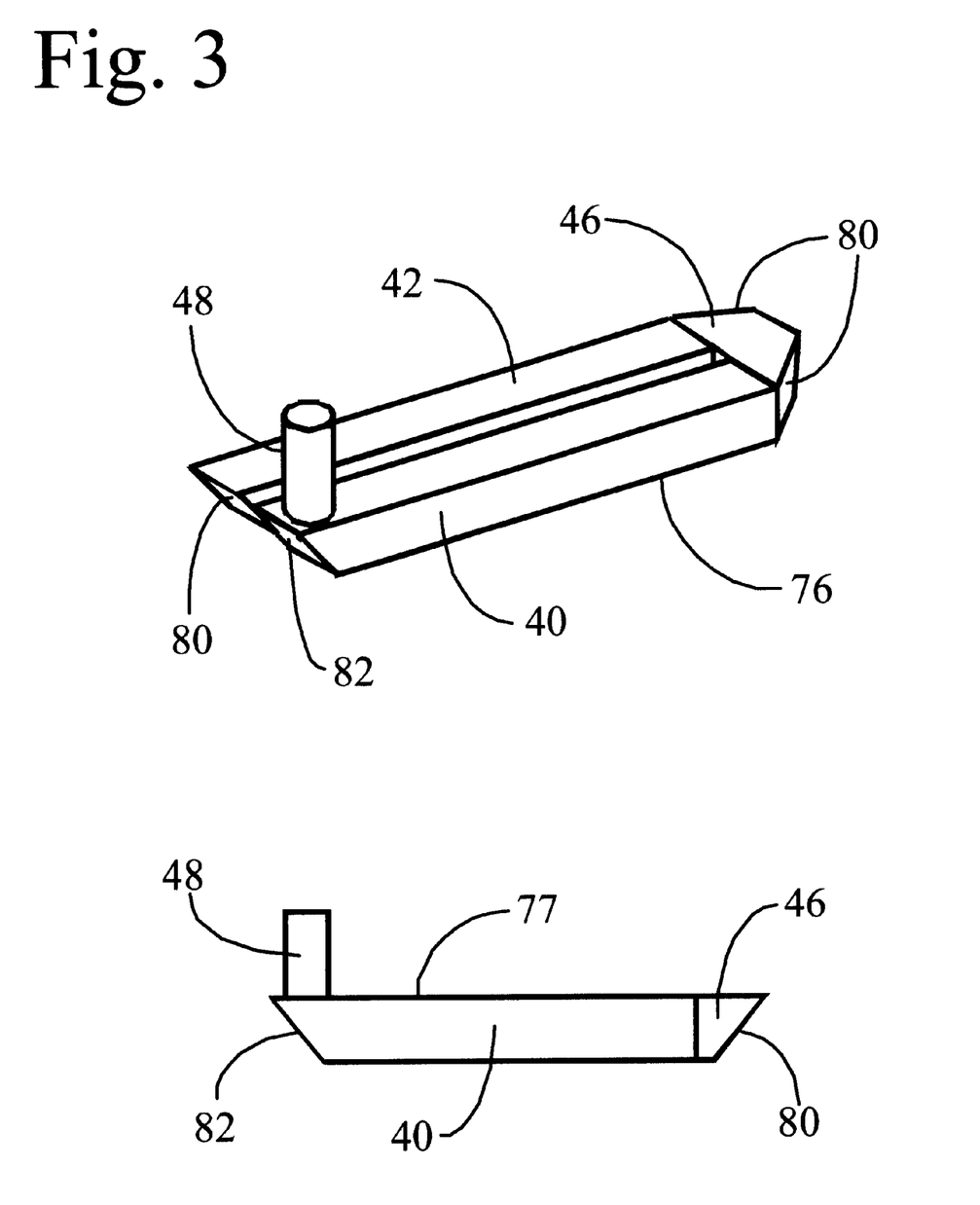
FIG. 3 is a perspective view illustrating a backscatter detector.

Alternatively, as shown in FIG. 3, backscatter detector 76 comprises two elongated scintillator sections optically linked to at least one photon detector. Each of the scintillator sections is oppositely disposed along pencil beam entrance slit 27. Scintillator segments 40 and 42 are joined via a simple light pipe block 46. The light is guided through light pipe block 46 via two 45 degree cuts 80 at the scintillator segment ends touching block 46. The pickup end of segment 40 has an approximation of a semi-paraboloid 82. Scintillator 42 has a 45 degree wall 80 for reflection improvement. A perspective view of the detector is shown as 76 in FIG. 3, while a side view is shown as 77.

As a further option, two distal backscatter detectors 18 and 19 are employed and positioned to bracket backscatter detectors 12 and 13, as shown in FIGS. 1 and 2. Preferably, the fast backscatter detectors 18 and 19 are comprised of scintillators 50 and 52 and photon detectors 58 and 59, respectively. Scintillators 50 and 52 are comprised of organic plastic. Photon detectors 58 and 59 are preferably photomultipliers. Alternatively, scintillators 50 and 52 are comprised of short persistence phosphor such as $Gd_2SiO_5$ or $Y_2O_2Si$.

From the portion of pencil beam 26 which is scattered from object 15, most of the backscatter will hit one of the backscatter detectors. Scattered radiation which originates from the top of object 15 is picked up rather equally by all backscatter detectors, while scattered radiation which originates closer to the bottom of object 15 shows up mainly in the detectors 40 and 42.

Figure 4:
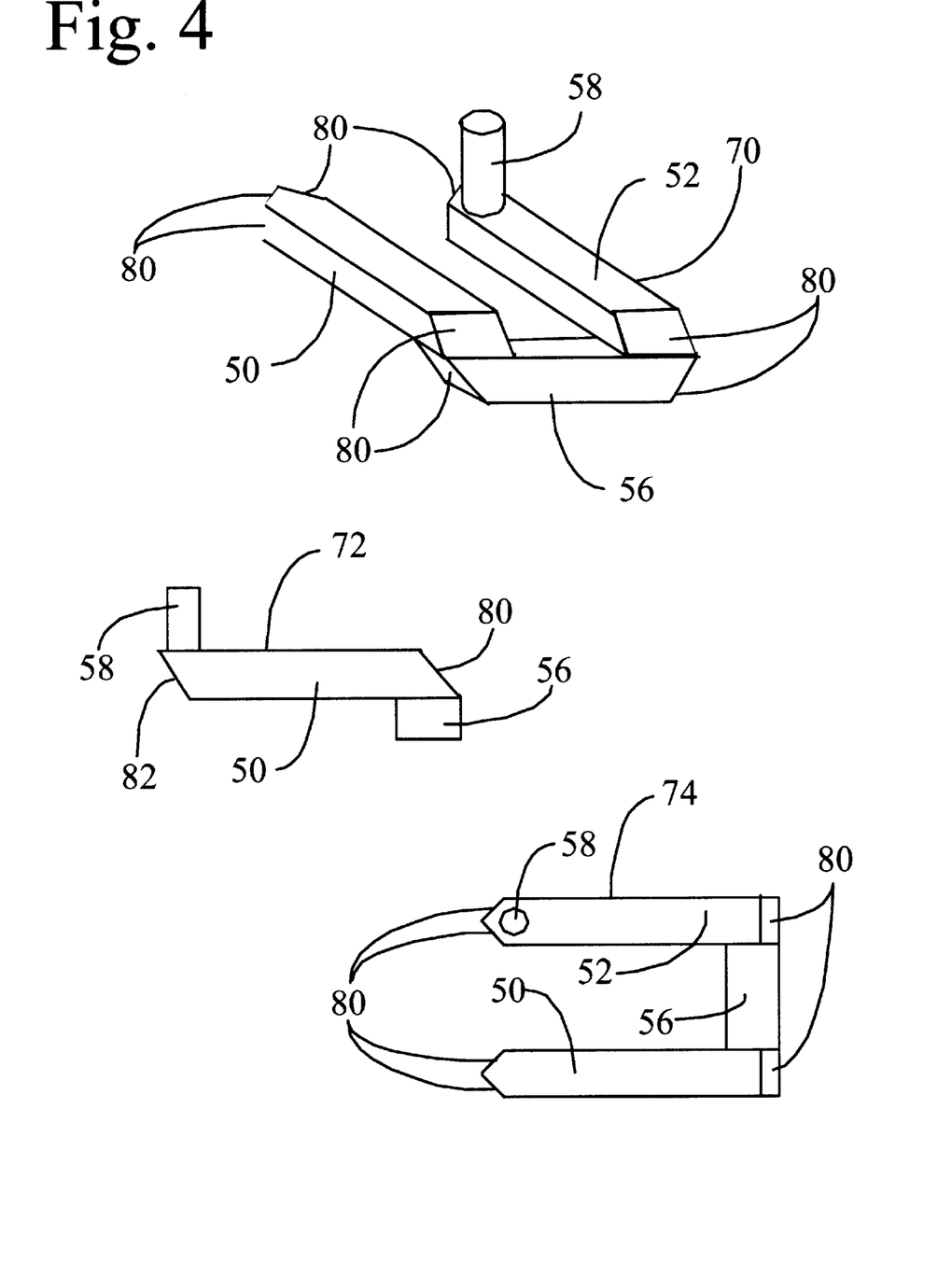
FIG. 4 depicts various views of an alternate embodiment for a backscatter detector.

A further alternative is illustrated by FIG. 4. Distal backscatter detectors 18 and 19 are combined 70 and comprise two elongated scintillators 50 and 52. The scintillators are optically linked via light pipe 56 to at least one photon detector 58. Each of the scintillators is oppositely disposed along pencil beam entrance slit 27. Preferably, the end of scintillator 52 having photon detector 58 is an approximate semi-paraboloid 82, while the other ends are provided with 45 degree cuts, shown as 80 in FIG. 5, to improve reflection. The two scintillators 50 and 52 are optically connected with light pipe 56 having cut ends 80 to improve reflection. In FIG. 4, a perspective view of the detector is shown at 70; side and top views are shown as 72 and 74, respectively.

These scintillators convert the backscatter x-ray energy reaching them into light photons. These light photons are conducted in the scintillators to their respective photomultiplier tubes, which convert the light photons into backscatter signals.

As shown in FIGS. 1 and 2, transmission detector 17 is used to generate a transmission signal when detecting X-rays 26 which are not absorbed or scattered by the object 15. The transmission detector 17 is positioned on the opposite side of object 15 as backscatter detectors 12 and 13. In this manner, object 15 moves between the transmission detector 17 and backscatter detectors 12 and 13. Preferably, transmission detector 17 is comprised of scintillators 30, 31, and 32 and photon detectors 38 and 39. Scintillators 30, 31, and 32 are comprised of organic plastic, and are arranged in a U shape, as shown in FIG. 2. Photon detectors 38 and 39 are preferably photomultipliers. Alternatively, scintillators 30, 31, and 32 are comprised of short persistence phosphors such as $Gd_2SiO_5$ or $Y_2O_2Si$.

Figure 5:
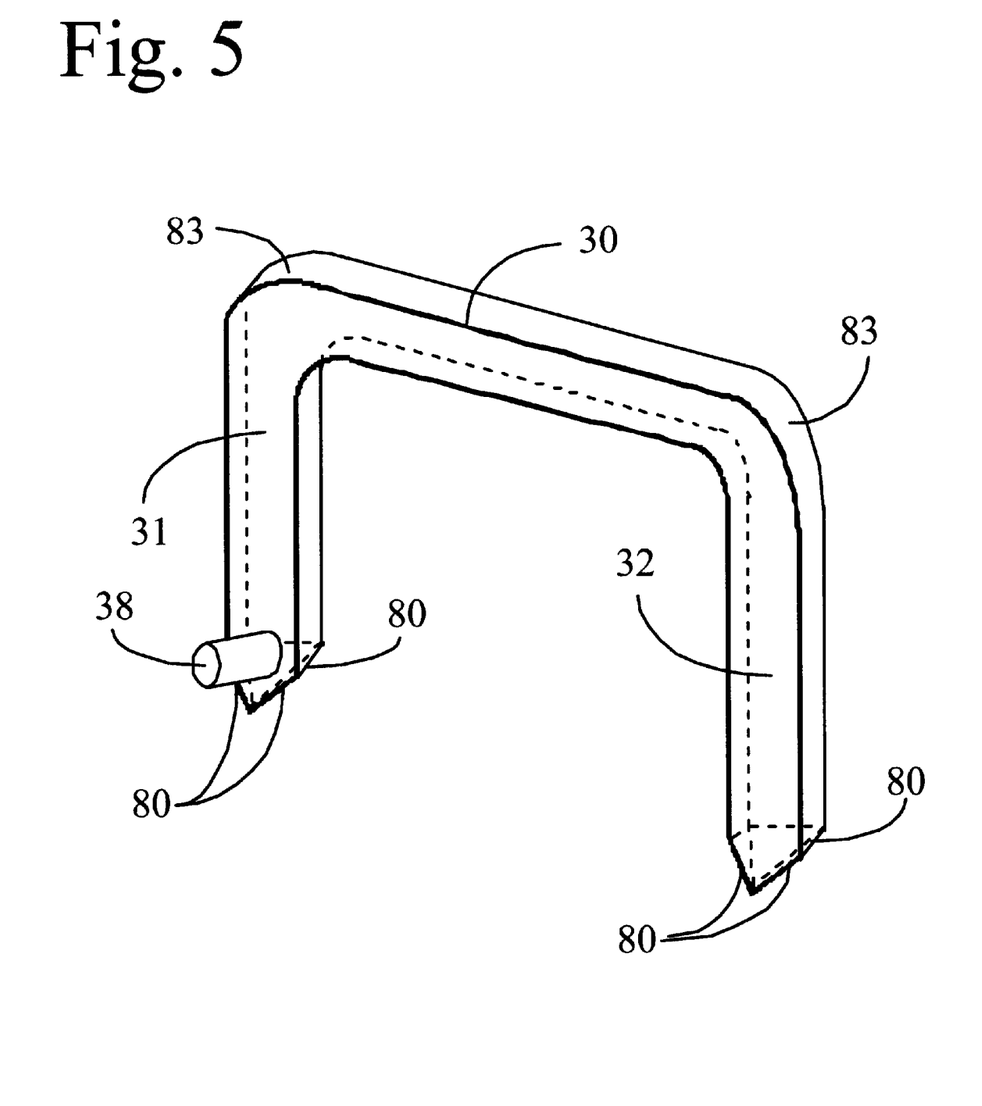
FIG. 5 shows various views for an alternate embodiment for a transmitted radiation detector.
Figure 6:
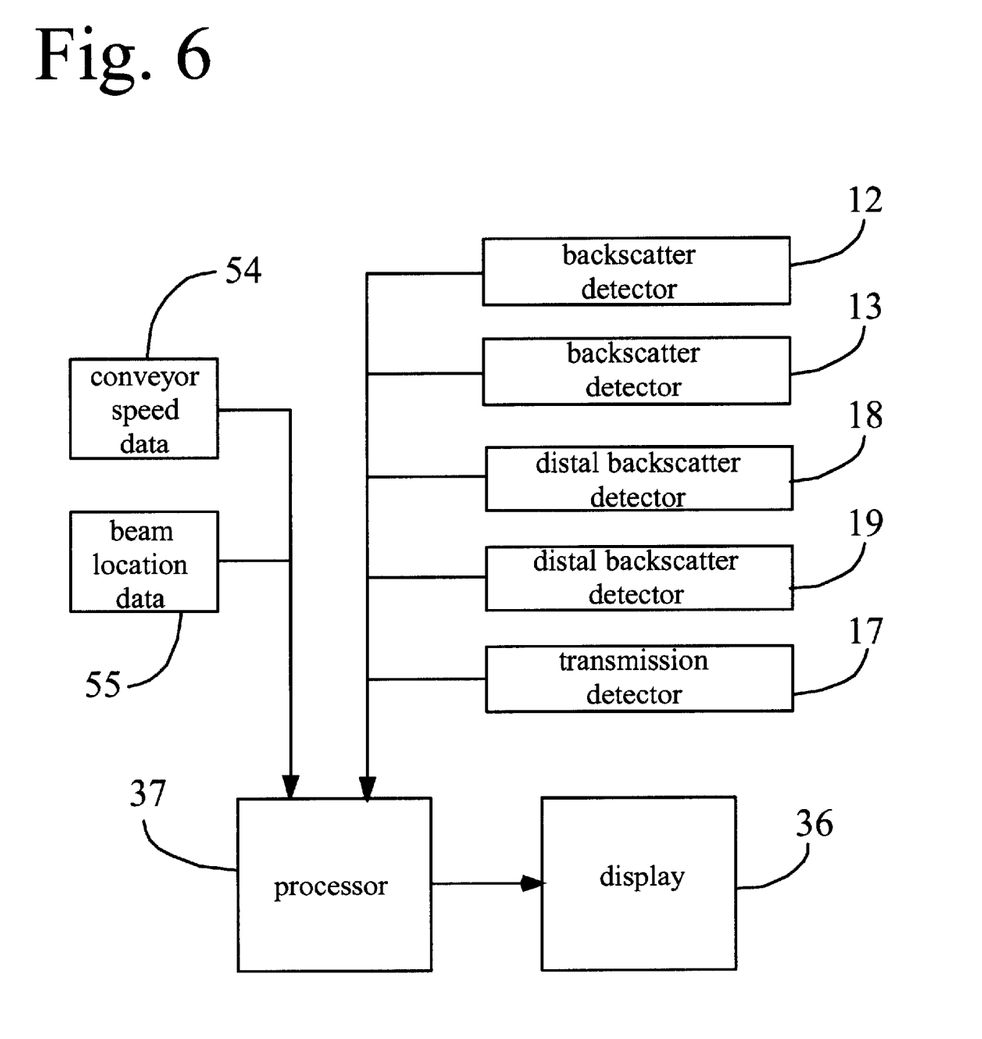
FIG. 6 is a block diagram illustrating signal flow for the system of FIG. 1.

FIG. 5 shows a U shaped transmission detector 17 comprised of scintillators 30, 31, and 32. Detector 17 is provided with rounded corners 83 generating a constant cross section for the whole detector. Preferably, corners 83 may be divided into a plurality of fibers or laminated to minimize light losses. A constant cross section, also called adiabatic, has the least losses for light conduction via total reflection. Photodetector 38 is located at one end of a segment. Preferably, this pickup end has the shape of a semi-paraboloid. That shape focuses more radiation than any other shape into photodetector 38, mounted atop the focal point of the semi-paraboloid. Alternatively, a multifaceted approximation of a semi-paraboloid is used in place of the difficult to make semi-paraboloid. As a further alternative, there is used a minimum of just two facets at 45 degree in space, as shown in FIG. 6. The opposite end of the segment—the end without the photodetector—has two 45 degree walls which reflect most of the light back into the segment by total reflection.

Scintillators 30, 31, and 32 convert most of the x-ray energy reaching them into light photons. These light photons are conducted in the scintillators to photomultiplier tubes 38 and 39, which convert the light photons into transmission signals.

Referring to FIG. 6, processor 37 processes the backscatter and transmission signals received from their respective detectors into tomographic information for display on display means 36. Preferably, display means 36 is a CRT or LCD display. Processor 37 is automatically switchable between photon counting and photon integration modes. Optionally, the switching is accomplished manually. Pencil beam location data 55 provides processor 37 with information on the location of the beam. Speed data 54 provides processor 37 with information on the speed of conveyor 10.

The reconstructed images of the transmission signal, backscatter signal, and the distal backscatter signal can be displayed separately or as a combined image showing suspicious material as a colored area.

Figure 7:
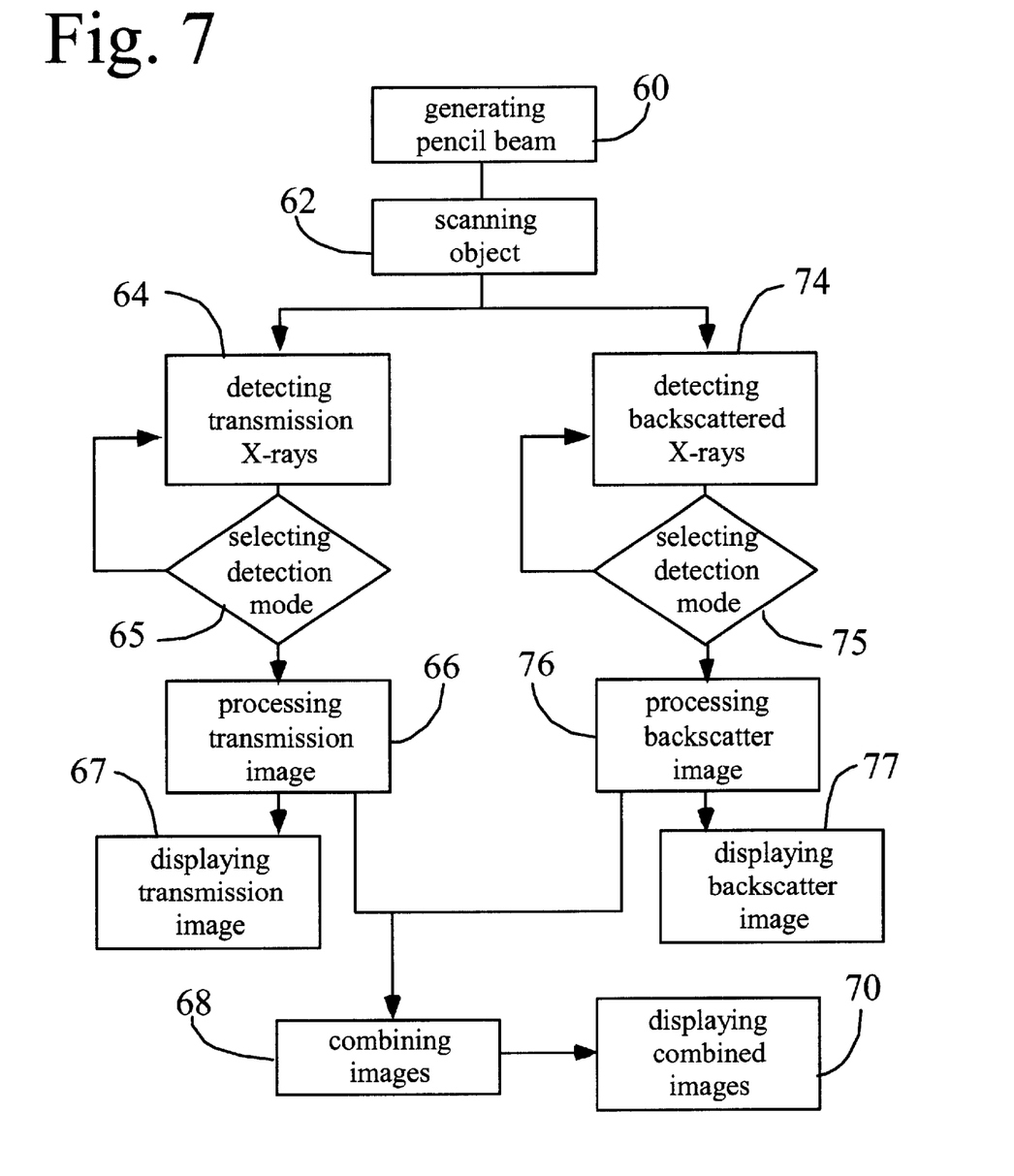
FIG. 7 is a block diagram depicting the method for X-ray inspection of an object using transmitted and Compton backscattered radiation.

The method to carryout X-ray inspection of an object using transmitted and Compton backscattered radiation is shown in FIG. 7. A pencil beam of X-rays is generated 60 and scanned 62 across the object to be inspected. X-rays transmitted through the object are detected 64 using a fast transmission detector. A mode of detection 65 is selected from either photon integration or photon counting. X-rays backscattered from the object are detected 74 using a fast backscatter detector, and a mode of detection 75 is selected from either photon integration or photon counting. Optionally, mode selection is omitted for the backscatter image. Next, a transmission image is processed 66 from the detected transmission X-rays and displayed 67. A backscattered image is processed 76 from the detected backscattered X-rays and displayed 77. Optionally, the processed transmission and backscatter images are combined 68 and displayed 70 as a composite image.

Additional scintillation detectors at the top and sides, in close proximity with the scintillation detectors for the transmitted radiation, create additional tomographic layers of resolution and improve the transmission image. The improvement is especially advantageous for high attenuation of the transmitted radiation. The forward scatter is measured and used as a correction for the transmitted radiance detector, which automatically captures forward scatter together with the transmitted radiation. Since the transmission scintillator detector system is divided into sections, those sections which are not currently collecting transmission image information can be used to collect scattered X-rays in the forward direction. The detection of these scattered X-rays can be used to improve the backscatter image or used to create an additional tomographic layer.

Figure 8:
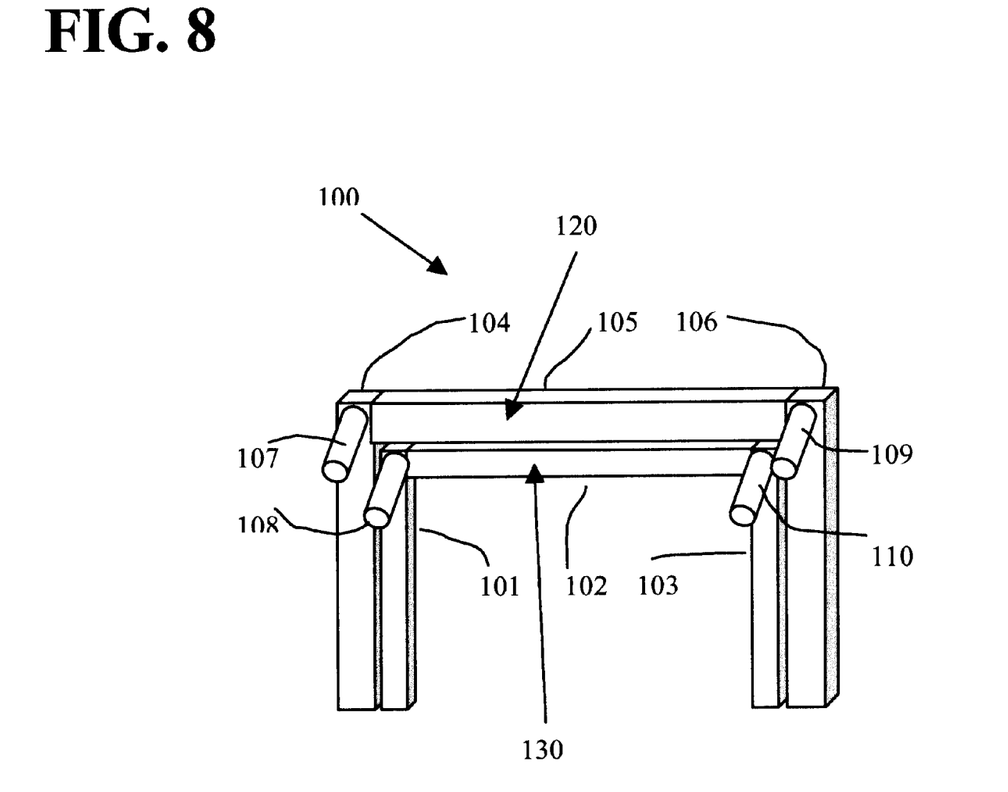
FIG. 8 is a perspective view illustrating a dual energy transmitted radiation detector for providing a dual energy image containing radiographic density and atomic number information of an object under inspection.

In FIG. 8 there is shown a detector configuration 100 for obtaining dual energy information by properly adjusting the thickness of inner transmission detector 130 and outer transmission detector 120. Inner detector 130 is U shaped, and comprises scintillators 101, 102, and 103, as well as photodetectors 108 and 110. Outer detector 120 comprises scintillators 104, 105 and 106, as well as photodetectors, 107 and 109. Preferably, corners are divided into a plurality of fibers or laminated to minimize light losses, as described in connection with detector 17 (see FIG. 5). The transmitted pencil X-ray beam first interacts with the inner detector 130, and by selecting the detector material and thickness it will preferably absorb lower energy. Material and thickness of outer detector 120 would be selected to absorb the higher energy X-rays that exit inner detector 130. Alternatively, a sheet of filtering material such as copper, steel or the like could be disposed between the inner detector 130 and outer detector 120 to increase discrimination between the high and low energy photons. The signal strengths of the inner and outer detectors are compared to determine the atomic number Z of the object. Further comparison of the dual energy information and scatter information will give a more accurate Z determination and aid in separating overlying materials.

Figure 9:
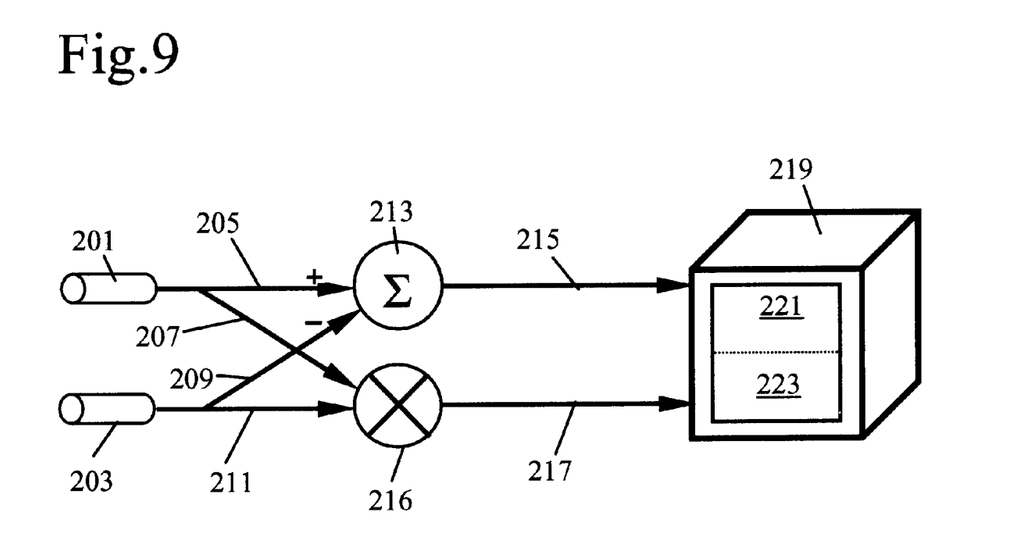
FIG. 9 is a diagrammatic view depicting a transmission detector and generated transmission signal, which is combined with a scatter correction signal in a summing device to produce and display a transmission signal in a transmission image window of a monitor.

In FIG 9 there is shown a transmission detector 201 generating transmission signal 205. The transmission signal 205 is combined with scatter correction signal 209 in summing device 213. A corrected transmission signal 215 is displayed in transmission image window 221 on monitor 219. Backscatter detector 203 generates backscatter signal 211, which is combined with attenuation correction signal 207 in multiplier 216. A corrected backscatter signal 217 is displayed in backscatter image window 223.

Having thus described the invention in rather full detail, it will be understood that such detail need not be strictly adhered to, but that additional changes and modifications may suggest themselves to one skilled in the art, all falling within the scope of the invention as defined by the subjoined claims.

We claim:

1. A scanning X-ray inspection system comprising:
   a) a conveyor for moving an object to be scanned though said system;
   b) an X-ray generation device for generating a pencil beam of X-rays repeatedly sweeping along a straight line across said conveyor, thereby scanning said object as it moves through said system;
   c) a fast backscatter detector for generating a backscatter signal when detecting said X-rays backscattered by said object moving on said conveyor, said backscatter detector being disposed on the same side of said moving object as said X-ray generation device and proximate to said straight line, and comprising two elongated scintillator sections optically linked to at least one photon detector, each of said sections being oppositely disposed along said straight line;
   d) a transmission detector for generating a transmission signal when detecting said X-rays traversing said object moving on said conveyor, said transmission detector being positioned on the opposite side of said object as said backscatter detector, whereby said object moves between said transmission detector and said backscatter detector;
   e) a processor for processing said backscatter and transmission signals for a display; and
   f) a display means for displaying a backscatter image and/or a transmission image.

2. A system as recited by claim 1, wherein said scintillator sections comprise a short persistence phosphor.

3. A system as recited by claim 2, wherein said short persistence phosphor is either $Gd_2SiO_5$ or $Y_2O_2Si$.

4. A system as recited by claim 2, wherein said scintillator sections comprise organic plastic scintillators.

5. A system as recited by claim 1, said system being a tomographic system and further comprising a second fast backscatter detector positioned along said straight line and opposite from said fast backscatter detector.

6. A system as recited by claim 1, said system being a tomographic system and further comprising a plurality of distal fast backscatter detectors for detecting X-rays scattered from the distal portion of said object, said distal fast backscatter detectors being disposed alongside said fast backscatter detector whereby said fast backscatter detector is positioned between said straight line and said distal fast backscatter detectors.

7. A system as recited by claim 1, wherein said processor is switchable between photon counting and photon integration modes.

8. A system as recited by claim 7, wherein said processor is automatically switchable between photon counting and photon integration modes.

9. A system as recited by claim 1, whereby said transmission detector comprises a scintillator having a short persistence phosphor and at least one photon detector.

10. A system as recited by claim 9, wherein said short persistence phosphor is either $Gd_2SiO_5$ or $Y_2O_2Si$.

11. A system as recited by claim 9, wherein said transmission detector comprises an organic plastic scintillator.

12. A scanning X-ray inspection system comprising:
    a) a conveyor for moving an object to be scanned though said system;
    b) an X-ray generation device for generating a pencil beam of X-rays repeatedly sweeping along a straight line across said conveyor, thereby scanning said object as it moves through said system;
    c) a fast backscatter detector for generating a backscatter signal when detecting said X-rays backscattered by said object moving on said conveyor, said backscatter detector being disposed on the same side of said moving object as said X-ray generation device and proximate to said straight line;
    d) a transmission detector for generating a transmission signal when detecting said X-rays traversing said object moving on said conveyor, said transmission detector being positioned on the opposite side of said object as said backscatter detector, whereby said object moves between said transmission detector and said backscatter detector, and said transmission detector comprising three elongated sections optically linked to at least one photon detector, said sections being linked to form three sides of an open rectangle;
    e) a processor for processing said backscatter and transmission signals for a display; and
    f) a display means for displaying a backscatter image and/or a transmission image.

13. A system as recited by claim 12, whereby said fast backscatter detector comprises a scintillator having a short persistence phosphor and at least one photon detector.

14. A system as recited by claim 13, wherein said short persistence phosphor is either $Gd_2SiO_5$ or $Y_2O_2Si$.

15. A system as recited by claim 13, wherein said fast backscatter detector comprises an organic plastic scintillator.

16. A system as recited by claim 12, said system being a tomographic system and further comprising a second fast backscatter detector positioned along said straight line and opposite from said fast backscatter detector.

17. A system as recited by claim 12, wherein said fast backscatter detector comprises two elongated scintillator sections optically linked to at least one photon detector, each of said sections being oppositely disposed along said straight line.

18. A system as recited by claim 12, said system being a tomographic system and further comprising a plurality of distal fast backscatter detectors for detecting X-rays scattered from the distal portion of said object, said distal fast backscatter detectors being disposed alongside said fast backscatter detector whereby said fast backscatter detector is positioned between said straight line and said distal fast backscatter detectors.

19. A system as recited by claim 12, wherein said processor is switchable between photon counting and photon integration modes.

20. A system as recited by claim 19, wherein said processor is automatically switchable between photon counting and photon integration modes.

21. A system as recited by claim 12, whereby said elongated sections comprise scintillators having a short persistence phosphor and at least one photon detector.

22. A system as by claim 21, wherein said short persistence phosphor is either $Gd_2SiO_5$ or $Y_2O_2Si$.

23. A system as recited by claim 12, wherein said elongated sections comprise organic plastic scintillators and at least one photon detector.

24. A backscatter detector for use in a tomographic scanning X-ray inspection system, comprising:
 a) an organic plastic scintillator having one end formed as a semi-paraboloid; and
 b) a photomultiplier tube mounted at the focus of said semi-paraboloid.

25. A transmission detector for use in a tomographic scanning X-ray inspection system, comprising:
 a) an organic plastic scintillator having the shape of a U, one end of which is formed as a semi-paraboloid; and
 b) a photomultiplier tube mounted at the focus of said semi-paraboloid.

* * * * *